United States Patent [19]

Oku et al.

[11] Patent Number: 5,789,165
[45] Date of Patent: Aug. 4, 1998

[54] METHOD AND REAGENT FOR SIMULTANEOUSLY ASSAYING ONE OR MORE LIGANDS IN A GROUP OF PRESELECTED LIGANDS

[75] Inventors: Yuichi Oku; Noriko Toyoda, both of Ibaraki, Japan

[73] Assignee: Nissui Pharmaceutical Co., Ltd., Japan

[21] Appl. No.: 535,248

[22] PCT Filed: Apr. 28, 1994

[86] PCT No.: PCT/JP94/00725
§ 371 Date: Oct. 30, 1995
§ 102(e) Date: Oct. 30, 1995

[87] PCT Pub. No.: WO94/27150
PCT Pub. Date: Nov. 24, 1994

[30] Foreign Application Priority Data

May 10, 1993 [JP] Japan ..................... 5-132739

[51] Int. Cl.$^6$ ..................... C12Q 1/68
[52] U.S. Cl. ............ 435/6; 435/7.1; 435/7.92; 435/7.94; 435/962; 435/971; 435/973; 435/975; 436/518; 436/538; 436/541; 436/808; 436/824
[58] Field of Search .............. 435/6, 7.1, 7.94, 435/7.92, 962, 971, 973, 975; 436/538, 541, 824, 808, 518

[56] References Cited

U.S. PATENT DOCUMENTS

| | | | |
|---|---|---|---|
| 4,748,111 | 5/1988 | Dattagupta et al. | 435/7 |
| 4,778,751 | 10/1988 | El Shami et al. | 435/971 X |
| 5,120,662 | 6/1992 | Chan et al. | 436/530 |
| 5,356,772 | 10/1994 | Chan et al. | 435/5 |

FOREIGN PATENT DOCUMENTS

| | | |
|---|---|---|
| 60-226900 | 11/1985 | Japan. |
| 63-36151 | 2/1988 | Japan. |
| 63-188399 | 8/1988 | Japan. |
| 4-204379 | 7/1992 | Japan. |
| 4-232465 | 8/1992 | Japan. |

OTHER PUBLICATIONS

Microbiol. Immunol. vol. 32(8), 807–816, 1988.
J. Biochem 108, 960–964 (1990).

*Primary Examiner*—Carol A. Spiegel

[57] ABSTRACT

The assay reagent and kit of the present invention suppress non-specific binding of a labeled substance onto a solid phase, and can assay one or more species of antibodies or one or more species of antigens by means of a single reagent in a simple manner. The assay method involves reacting immunological ligands in a test sample with the assay reagent which contains a combination of components (A) and (B), thereby forming complexes, which complexes are captured onto the independently and separately present Solid phases (C), to assay the label contained in the complexes. Component (A): one or more species of immunological anti-ligand-nucleotide conjugates, in each of which nucleotides with a specific base sequence, independently selected depending on the species of an immunological ligand, are bound to an immunological anti-ligand having a specific immunological affinity to one of the different species of immunological ligands to be assayed; (B): labeled substances each having a specific affinity to one of the different species of immunological ligands to be assayed; Solid phase (C): solid phase-nucleotide conjugates wherein nucleotides, each having a base sequence complementarily binding to a nucleotide of the above component (A), are immobilized onto a water-insoluble support. Either an antigen or an antibody may serve as the aforementioned immunological ligand and immunological anti-ligand.

20 Claims, 11 Drawing Sheets

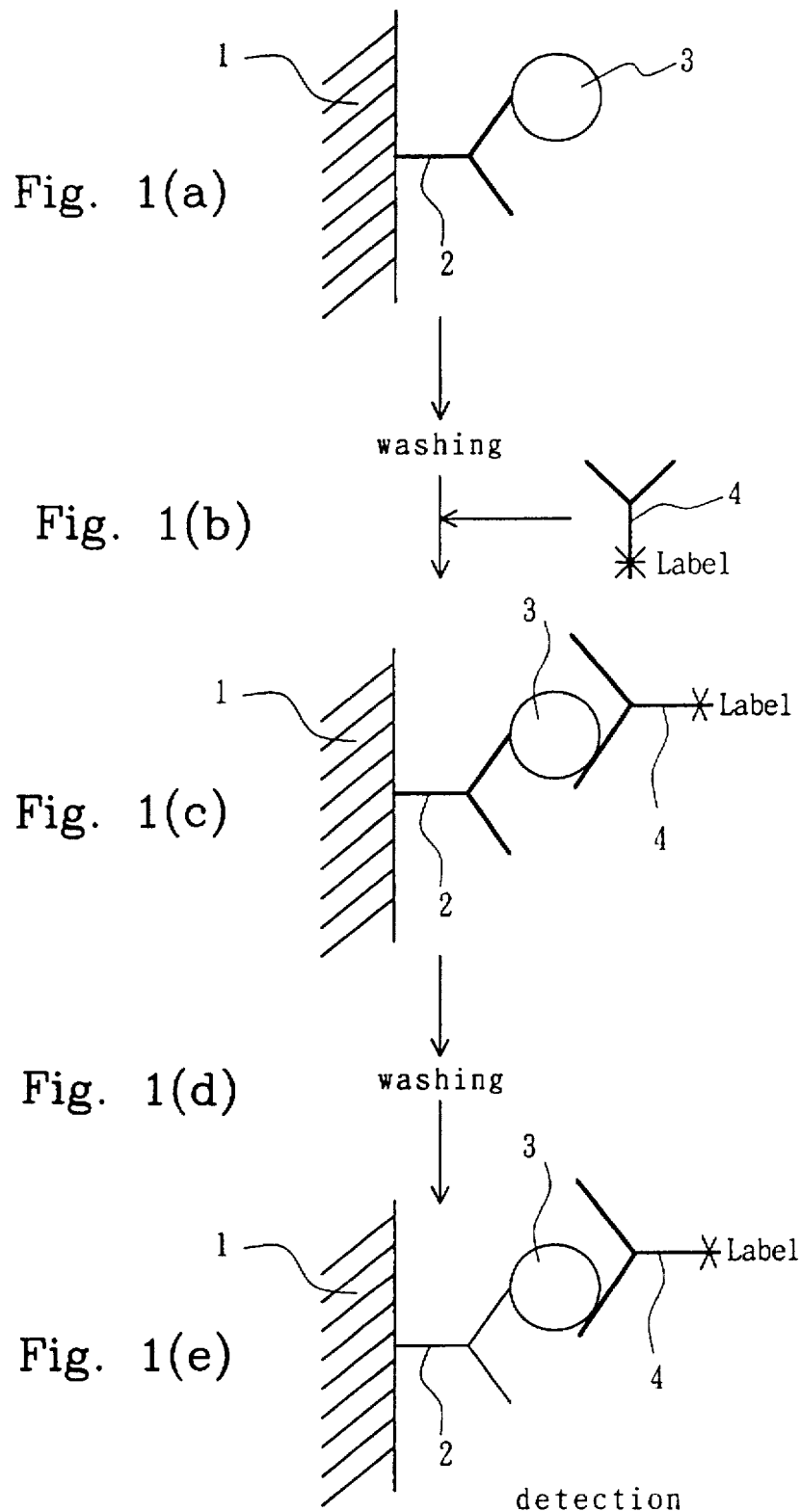

Fig. 2

Antigen assay reagent capable of assaying concurrently Antigen A,B,C

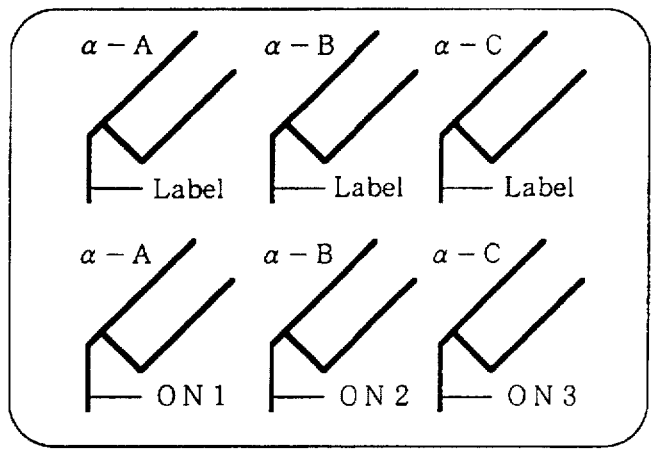

α−A, B, C : Antibodies against Antigen A,B,C, respectively

ON 1 : Oligonucleotide having a base sequence different from those of other Nucleotides ON2 and ON3

ON 2 : Oligonucleotide having a base sequence different from those of other Nucleotides ON1 and ON3

ON 3 : Oligonucleotide having a base sequence different from those of other Nucleotides ON1 and ON2

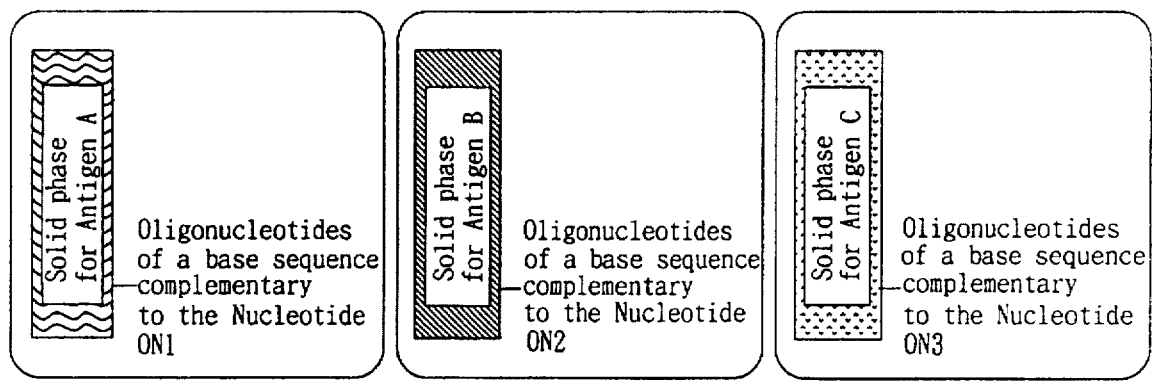

Antibody assay reagent capable of assaying concurrently Antibody A,B,C

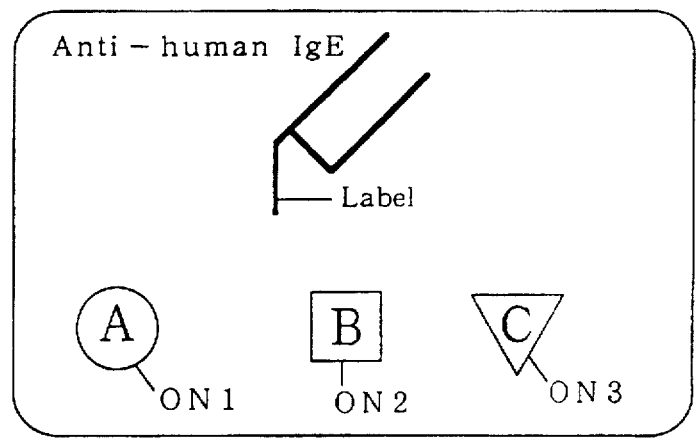

A, B, C : Antigen A,B,C, respectively

ON 1 : Oligonucleotide having a base sequence different from those of other Nucleotides ON2 and ON3

ON 2 : Oligonucleotide having a base sequence different from those of other Nucleotides ON1 and ON3

ON 3 : Oligonucleotide having a base sequence different from those of other Nucleotides ON1 and ON2

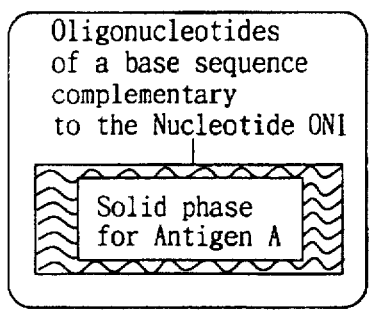

Fig. 12(a)

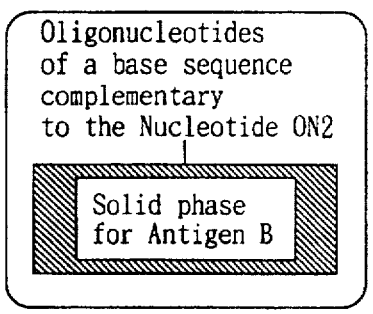

Fig. 12(b)

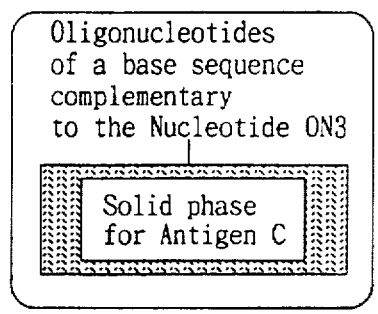

Fig. 12(c)

METHOD AND REAGENT FOR SIMULTANEOUSLY ASSAYING ONE OR MORE LIGANDS IN A GROUP OF PRESELECTED LIGANDS

This is a U.S. National Phase Application under 35 USC 371 based on PCT/JP94/00725 and claimed priority of Japanese Application 05-132739 filed May 10, 1993.

BACKGROUND OF THE INVENTION

1. Field of the Invention

The present invention relates to a method for immunologically assaying biological substances using an antigen-antibody reaction. More specifically, the present invention relates to a method for assaying one or more species of antigens or one or more species of antibodies, characterized in that the method is capable of assaying an almost infinite number of combinations of one or more species of antigens or one or more species of antibodies, an assay reagent using the same and a kit using the same.

2. The Prior Art

Immunoassays have been used in the field of clinical diagnosis for assaying and detecting a trace of biological substances, and a variety of methods have been developed therefor. Because immunoassays use non-radioactive substances such as fluorescent substances, luminescent substances and enzymes as labels for antibodies, and therefore, do not require special equipment as is required when a radioactive substance is used as a labeling substance, such assays have been more widely used than other methods for assaying biological substances. Such immunoassays offer easy handling of the reagents and the processability of a great number of samples.

By such immunoassays, generally, only a single antigen may be assayed or detected in a single clinical sample. When a plurality of antigen species are present in a sample which are defined as Antigens A, B and C, for example, a specific reagent for selectively detecting the Antigen A is required, which is also the case with the Antigens B and C. Thus, these antigens each require its own specific reagent for assay. Generally, a number of clinical test results are integrally required for clinically diagnosing the disease of a patient. So as to receive appropriate treatment under appropriate diagnosis, accordingly, a patient generally should be subjected to a plurality of clinical tests. For that reason, in most cases, the volume of a sample collected from a patient increases in proportion to the number of clinical tests required for that patient, which is a bodily burden for the patient. As a response to demand to decrease such burden, no satisfactory assay method, simple and highly sensitive, is currently available.

As an immunoassay method to simultaneously determine the presence and/or level of two or more species of antibodies in a sample, dot blotting has conventionally been used, for example, as disclosed in Japanese Patent Laid-Open No. Hei 4-232465 (1992). Dot blotting comprises preliminarily spotting various species of antigens on a nitrocellulose membrane, reacting a sample possibly containing a plurality of antibodies to be detected with the antigens on the nitrocellulose membrane, and subsequently binding a labeling substance to the antibodies captured on the nitrocellulose membrane to detect the presence or level of the antibodies. However, such dot blotting for detecting two or more species of antibodies is problematic in that the entire process thereof requires a long time and also requires a larger volume of a sample. Furthermore, the dot blotting method has a problem in that since antigens should be immobilized onto a solid phase for use in assaying antibodies, the immobilized antigens deteriorate during storage.

FIGS. 1(a)–1(e) depict the scheme of the general process of another immunoassay method which is different from dot blotting, which is called a sandwich assay and which is one of the conventional immunoassay methods using a labeled compound.

Conventional sandwich assays by means of a labeling compound will now be described with reference to FIGS. 1(a)–1(e), wherein 1 represents solid phase of a water-insoluble support; 2 represents antibody immobilized onto the solid phase; 3 represents an antigen to be assayed, which has reacted with the antibody and then bound to the antibody; and 4 represents a labeled antibody.

By bringing a test sample into contact with antibody 2 immobilized onto solid phase 1, the antigen to be detected in the test sample should become bound to the antibody 2 (FIG. 1(a)). So as to remove the unreacted contaminants from the reaction system, washing is carried out (FIG. 1(b)). Labeled antibody 4 reacts with the solid phase-antibody-antigen complex, to form a solid phase-antibody-antigen-labeled antibody complex (FIG. 1(c)). Washing is carried out so as to remove the contaminants such as unreacted labeled antibody and the like from the reaction system after completion of the above process (FIG. 1(d)). By detecting the label, the washed solid phase-antibody antigen-labeled antibody complex is determined (FIG. 1(e)).

By such general immunoassay methods, the labeled antibody responsible for the determination is derived from the solid phase-antibody-antigen-labeled antibody complex. Additionally, so-called non-specific binding of the labeled antibody directly onto the solid phase sometimes occurs, and in such case, the assay sensitivity suffers.

Many pathogenic factors such as specific hormones, tumor markers and bacteria are present at a trace level in samples. For the assay or detection then, a highly sensitive assay system has been required and developed (see for example Enzyme immunoassay, Eiji Ishikawa eds., Igaku Shoin, 1987; Microbiol. Immunol., Y. Oku et al, 32, pp. 807–816, 1988). The major problem in constructing the highly sensitive assay system is non-specific binding of the labeled antibody onto the solid phase.

For the purpose of eliminating such non-specific binding, immune complex transfer assay (J. Biochem., S. Hashida et al., 108, pp. 960–964, 1990) and like methods, have been developed to attain practically higher sensitivity than those of conventional assays. The immune complex transfer assay comprises the following steps. More specifically, the assay comprises simultaneously mixing an antibody conjugated with a dinitrophenyl group (referred to as "IDNP" group) and biotin, the antibody recognizing a specific antigen, a test sample, and an enzyme-labeled antibody recognizing the antigen, to obtain reaction of the antigen contained in the testing sample with the individual antibodies to form an immune complex (referred to as "IC" hereinafter ). An alternative method includes immobilizing an antibody against DNP group onto a solid phase, bringing the preliminarily prepared IC into contact with the solid phase to promote the antigen-antibody reaction between the DNP group contained in the IC and the antibody against DNP group on the solid phase, thereby capturing the IC on the solid phase.

Then, so as to exclude the effects of the non-specific binding of the enzyme-labeled antibody contained in the reaction system on the solid phase, the captured IC is released therefrom through the addition of an excess amount of a compound with a DNP group. Subsequently, the thus released IC is subjected to reaction with another solid phase immobilizing avidin, to again capture the IC on the solid phase, and then, the activity of the enzyme in the IC captured onto the solid phase is measured in a test tube, whereby the effects of the non-specific binding of the enzyme-labeled antibody on the solid phase can be eliminated, to attain high sensitivity. However, none of such conventionally known immune complex transfer assays provide detection and assay of plural species of antigens or plural species of antibodies by means of a single reagent.

Japanese Patent Laid-Open No. Sho 63-188399 (1988) describes a method for assaying a target molecule as a biological binding pair in a sample. Specifically, the publication describes that the assay procedure comprises bringing a sample containing a target molecule into contact with a first anti-ligand probe and a second labeled anti-ligand probe capable of bonding the target molecule to form a complex and a recoverable support, then substantially separating the recoverable support from the sample to recover an isolated product including the target molecule and the first and second probes in the presence of the target molecule in the sample, and further assaying the target product indicating the presence of the target molecule. However, the assay procedure described in the Japanese Patent Laid-Open No. Sho. 63-188399 does not describe the detection and assay of the presence of more than one species of antigens or more than one species of antibodies by means of a single reagent.

Additionally, Japanese Patent Laid-Open No. Hei 4-273065 (1992) describes a method for detecting an antigen contained in a sample at a high sensitivity, comprising preliminarily immobilizing an antibody through a nucleic acid onto a solid phase, capturing an antigen contained in a sample via the antigen-antibody reaction onto the solid phase, thereafter capturing a labeling substance thereon prior to washing, selectively cleaving the nucleic acid to separate and assay the separated labeling substance. However, Japanese Patent Laid-Open No. Hei 4-273065 does not teach anything about the detection and assay of more than one species of antigen or more than one species of antibody via a single reagent.

As has been described above, the entire process of the conventional dot blotting for detecting plural species of antibodies requires a long time and additionally requires a relatively larger volume of a sample.

Because the reaction for capturing the labeled antibody onto the solid phase is an antigen-antibody reaction in the conventional immunoassay method as depicted in FIGS. 1(a)-1(e), the time required for capturing the labeled antibody onto the solid phase is relatively long. Thus, the duration of the labeling substance of the reaction system being exposed to the solid phase is so prolonged that so-called non-specific binding of the labeling substance directly onto the solid phase becomes problematic with decrease in assay sensitivity.

Furthermore, the conventional immune complex transfer assay methods intended for higher sensitivity require a greater number of complex assay procedures as well as a long time for those reactions, which is the principal drawback.

SUMMARY OF THE INVENTION

It is thus a first objective of the present invention to suppress to a minimum the occurrence of non-specific binding onto a solid phase of a labeling substance added to a reaction system, which disadvantageously causes a decrease of assay sensitivity. In addition to the first objective, furthermore, it is a second objective of the present invention to provide an assay reagent which can detect more than one species of antibodies or more than one species of antigens by means of a single reagent by a simple procedure, a kit using the same and an assay method using the same.

So as to overcome the problems described above, the present invention provides an assay reagent for assaying more than one species of immunological ligands, which concurrently contains the following reagents (A) and (B):

(A): plural species of immunological anti-ligand-nucleotide conjugates, in each of which nucleotides with a specific base sequence, independently selected depending on the species of an immunological ligand, are bound to an immunological anti-ligand having a specific immunological affinity to one of immunological ligands as different species of substances to be assayed; and (B): labeled substances each having a specific affinity to one of the different species of immunological ligands to be assayed.

Additionally, the present invention provides an assay kit for assaying one or more species of immunological ligands, comprising an assay reagent for assaying one or more species of immunological ligands which concurrently contains the following reagents (A) and (B), and the following solid phase reagent (C) which is independently separated from said assay reagent:

(A): one or more species of immunological anti-ligand-nucleotide conjugates, in each of which nucleotides with a specific base sequence, independently selected depending on the species of an immunological ligand, are bound to an immunological anti-ligand having a specific immunological affinity to one of different species of immunological ligands to be assayed.

(B): label substances each having a specific affinity to one of the immunological ligands as the different species to be assayed; and (C): solid phase-nucleotide conjugates wherein nucleotides having a base sequence complementarily binding to the nucleotides of the reagent (A) are immobilized onto a water-insoluble support.

In accordance with the present invention, the term "immunological ligand" means one molecule in an immunologically formed pair, while the term "immunological anti-ligand" means the other molecule in the immunologically formed pair. These immunological ligand and immunological anti-ligand pairs will include one antigen and one antibody.

The nucleotides having a complementary sequence in accordance with the present invention may be DNA or RNA. For such nucleotides, both of synthetic nucleotides and naturally occurring nucleotides may be used. The nucleotides may be oligonucleotides or polynucleotides.

An antibody-nucleotide conjugate or an antigen-nucleotide conjugate is bound to nucleotides immobilized on a solid phase via the complementary pairing of the base sequences of these nucleotides. Their complementary base sequences may be partially or wholly complementary as long as the nucleotide molecules thereof can bind to each other.

Generally, the complementary pairing of nucleotides characteristically has such a high specificity that the time required for such complementary pairing is far shorter than the time required for the formation of an antigen-antibody complex.

In accordance with the present invention, the time required for binding an antibody-nucleotide conjugate or an antigen-nucleotide conjugate to a solid phase immobilizing other nucleotides is far shorter than the time required for binding a labeled substance to a complex of a solid phase immobilizing an antibody thereon and an antigen (an antibody-bound solid phase-antigen complex) in accordance with the conventional immunoassay.

Because a labeled substance, for example, a labeled antibody, is not given sufficient time for directly binding to a solid phase in accordance with the present invention, non-specific binding can be decreased to attain a highly sensitive assay system.

In accordance with the present invention, furthermore, only a single reagent is capable of detecting or assaying one or more species of immunological ligands, namely antigens or antibodies, so that the time required for their detection or assay is markedly shortened, compared with the conventional methods.

As to the solid phase-nucleotide conjugate used as the Solid phase (C), the nucleotides may be covalently bonded at position 5' terminus or 3' terminus or at an optional position other than the termini onto a water-insoluble support, directly or through a functional group inserted into the water-insoluble support, to form a solid phase-nucleotide conjugate as the Solid phase (C). A functional group thus inserted into a solid phase may be covalently bonded to a functional group inserted into a base constituting a nucleotide, to form a covalent bond.

As another method for binding nucleotides onto a solid phase, physical adsorption may be adopted instead of covalent bonding for such binding. More specifically, nucleotides are covalently bonded, at position 5' terminus or 3' terminus or an optional position other than such termini onto a bonding ligand, directly or through a functional group inserted into the bonding ligand, to form a bonding ligand-nucleotide conjugate, which is then physically adsorbed onto a water-insoluble support to form a solid phase-nucleotide conjugate as the Solid phase (C). Preferably, the bonding ligand is a protein.

For labelling in the assay reagent in accordance with the present invention, use may be made of an enzymatically active atomic group, biotin, avidin, digoxigenin, nucleotides, a metal colloid particle, a fluorescent substance, a luminescence substance, a metal compound, a ligand with a specific binding affinity, or a radioisotope. The solid phase used in accordance with the present invention is preferably polystyrene.

The method for assaying plural species of immunological ligands in accordance with the present invention will now be explained with reference to FIGS. 2 to 10, wherein an antigen is illustrated as the immunological ligand to be assayed.

FIG. 2 depicts one example of the case wherein the assay reagent for assaying plural species of immunological ligands is an assay reagent for assaying plural species of antigens which are schematically depicted as antigens A, B and C. In FIG. 2, those in frame all represent the components contained in a single reagent. In FIG. 2, α-A, α-B and α-C represent antibodies against Antigens A, B and C, respectively.

The Antibodies α-A, α-B and α-C, each bound with a label, are thus prepared as label-modified substances, so the reagent thus simultaneously contains the three types of labeled antibodies. Concurrently with the aforementioned three types of labeled-antigen, the reagent further contains three types of antibody-nucleotide complexes wherein the antibody components are α-A, α-B and α-C, which are independently bound with different sequences of Nucleotides, ON1, ON2 and ON3, in this order. The Nucleotide ON1 has a base sequence different from those of Nucleotides ON2 and ON3. The Nucleotide ON2 has a base sequence different from those of Nucleotides ON1 and ON3. The Nucleotide ON3 has a base sequence different from those of Nucleotides ON1 and ON2.

Nucleotides of one base sequence should all be bound to the identical species of antibody. In accordance with the present invention, polyclonal antibodies are also encompassed in the terminology "identical species of antibody."

FIGS. 3(a)–3(c) depict one example of an admixture of solid phases with attached nucleotides, for use in combination the assay reagent for assaying one or more species of antigens in accordance with the present invention. FIG. 3(a) depicts a solid phase with attached nucleotides (ON) of a base sequence complementary to the Nucleotide ON1 (Solid phase for Antigen A); FIG. 3(b) depicts a solid phase with attached nucleotides (ON) of a base sequence complementary to the Nucleotide ON2 (Solid phase for Antigen B); and FIG. 3 (c) depicts a solid phase with attached nucleotides (ON) of a base sequence complementary to the Nucleotide ON3 (Solid phase for Antigen C). These different types of individual solid phases are independently and separately used in combination with the assay reagent for assaying plural species of antigens. These individual solid phases constitute one component of the assay kit in accordance with the present invention.

When the assay reagent of FIG. 2 is added to a test sample containing the Antigens A, B and C, complexes of (antibody-nucleotide conjugate)-antigen-labeled substance, individually corresponding to the Antigens A, B and C, form in the reaction solution as depicted in FIG. 4.

Then, bringing the reaction solution containing the complexes of (antibody-nucleotide conjugate)-antigen-labeled substance, into contact with the Solid phase for Antigen A, the Solid phase for Antigen B and the Solid phase for Antigen C, all of which phases are independently and separately present, the nucleotides contained in the complexes are complementarily paired through hybridization with the nucleotides of the Solid phases for Antigens A, B and C, having base sequences complementary to those of the nucleotides contained in the above complexes as depicted in FIG. 5, FIG. 6 and FIG. 7, respectively.

By subsequently washing, impurities not captured onto any of the solid phases, for example labeled substances and the like, can be removed. FIG. 8, FIG. 9 and FIG. 10 depict the state of the complex carrying antigen A complementarily paired on the Solid phase for Antigen A, the state of the complex carrying antigen B complementarily paired on the Solid phase for Antigen B, and the state of the complex carrying antigen C complementarily paired on the Solid phase for Antigen C, after washing, respectively. The labels contained in the complexes captured on the individual solid phases are next determined. For example, enzyme reactions are promoted in each independent reaction system to determine the level of the label via individual colors and the like. When the labels are fluorescent substances, dyes, metal colloids or the like, assay can be done without such enzyme reactions.

The above example illustrates a method for assaying antigens in a test sample, but the present invention also encompasses a method for assaying antibodies in a test sample. With reference to FIGS. 11 to 19, explanation will follow of the method for assaying plural species of antibodies as the immunological ligands to be assayed. FIG. 11 schematically depicts the assay reagent for assaying one or more species of antibodies, i.e. Antibodies A, B and C, and FIGS. 12(a)–12(c) illustrate one example of the nucleotide-bound solid phases to be used in combination with the assay reagents for assaying plural species of antibodies in accordance with the present invention. These different types of solid phases are independently and separately present. When combined with the assay reagent of FIG. 11, these individual solid phases constitute one example of an assay kit for assaying plural species of antibodies in accordance with the present invention.

When the assay reagent as depicted in FIG. 11 is added to a test sample containing Antibodies A, B and C, complexes of (antigen-nucleotide conjugate)-antibody-labeled substance are formed, individually for each of Antibodies A, B and C, in a single reaction solution as depicted in FIG. 13.

Then, the reaction solution containing the complexes of (antigen-nucleotide conjugate)-antibody-labeled substance is brought into contact with the independently and separately present Solid phases for Antibodies A, B and C, to prepare complementary pairs through hybridization between the nucleotides contained in the complexes and the nucleotides of the Solid phases of Antibodies A, B and C, having base sequences complementary to those of the nucleotides in the complexes. FIGS. 14, 15 and 16 depict the complexes captured via hybridization onto the individual solid phases.

By subsequent washing of the individual solid phases, impurities not attached onto the solid phases, for example, labeled substances, can be removed. In such manner, complexes captured on the individual three types of solid phases and from which impurities are removed, i.e. the complex carrying Antibody A, captured onto the Solid phase for Antibody A, as shown in FIG. 17, the complex carrying Antibody B, captured onto the Solid phase for Antibody B as shown in FIG. 18 and the complex carrying Antibody C, captured onto the Solid phase for Antibody C, as shown in FIG. 19, can be recovered individually.

The labels contained in the complexes captured onto the individual solid phases are next determined. For example, enzyme reactions and the like may be carried out in independent reaction systems, to determine the levels of the labels via color tones. When the labels are fluorescent substances, dyes and metal colloids and the like, assay can be done without such enzyme reaction.

The solid phase-nucleotide conjugate as the Solid phase C, for use in the assay reagent in accordance with the present invention, is stable in dry state and the conjugate can be stably stored even in solution in the presence of EDTA. Thus, the conjugate can be stably stored as a reagent.

BRIEF DESCRIPTION OF THE DRAWINGS

FIGS. 1(a)–1(e) depict the scheme of the general process of conventional immunoassay methods using labeled compounds;

FIG. 2 depicts one example of the assay reagent for assaying plural species of antigens A, B and C;

FIGS. 3(a)–3(c) depict one example of the solid phase bound with a nucleotide to be used in combination with the assay reagent for assaying plural species of antigens in accordance with the present invention;

FIG. 11 depicts one example of an assay reagent for assaying plural species of antibodies A, B and C;

FIGS. 12(a)–12(c) depict one example of solid phases bound with nucleotides to be used in combination with the assay reagent for assaying plural species of antibodies in accordance with the present invention;

DESCRIPTION OF THE PREFERRED EMBODIMENTS

[EXAMPLE 1]

Figure 4:
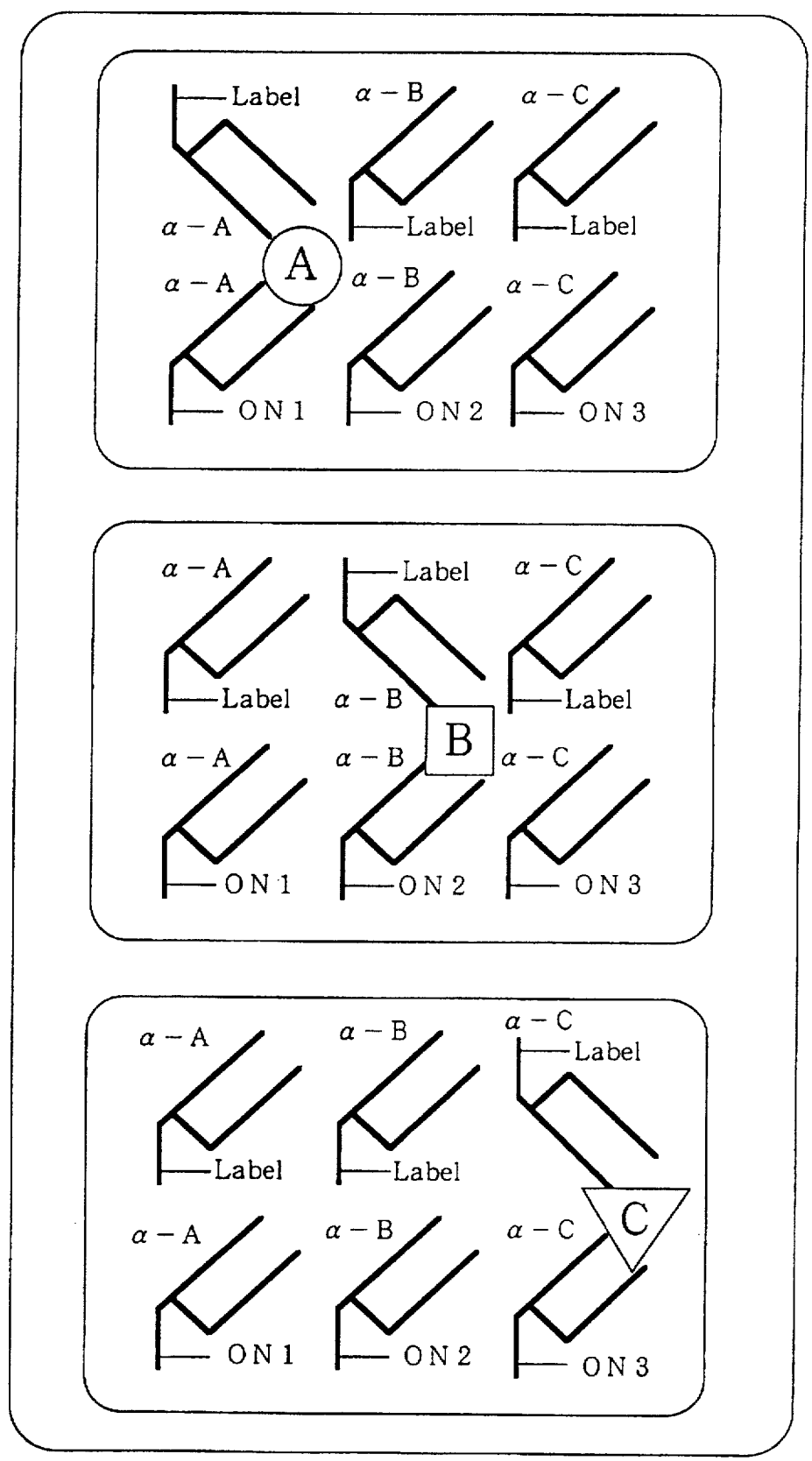
FIG. 4 depicts how the complex of (antibody-nucleotide conjugate)-antigen-labeled substance can be formed for plural species of antigens contained in a single reaction solution in accordance with the present invention.
Figure 5:
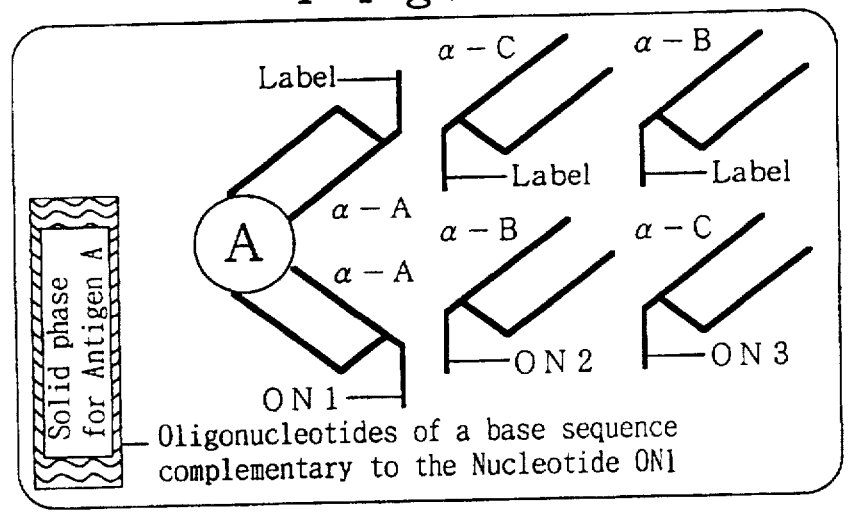
FIG. 5 depicts the state wherein a complex carrying Antigen A is captured through the complementary pairing of nucleotides onto the Solid phase for Antigen A in accordance with the present invention.
Figure 6:
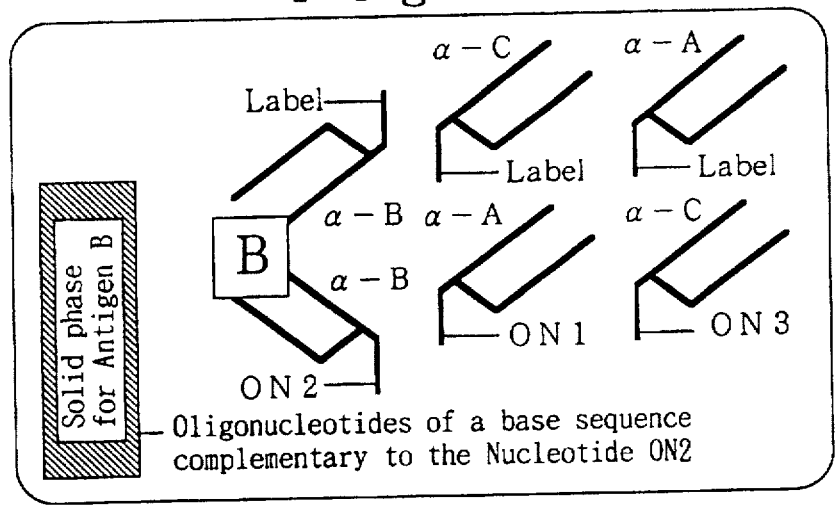
FIG. 6 depicts the state wherein a complex carrying Antigen B is captured through the complementary pairing of nucleotides onto the Solid phase for Antigen B in accordance with the present invention.
Figure 7:
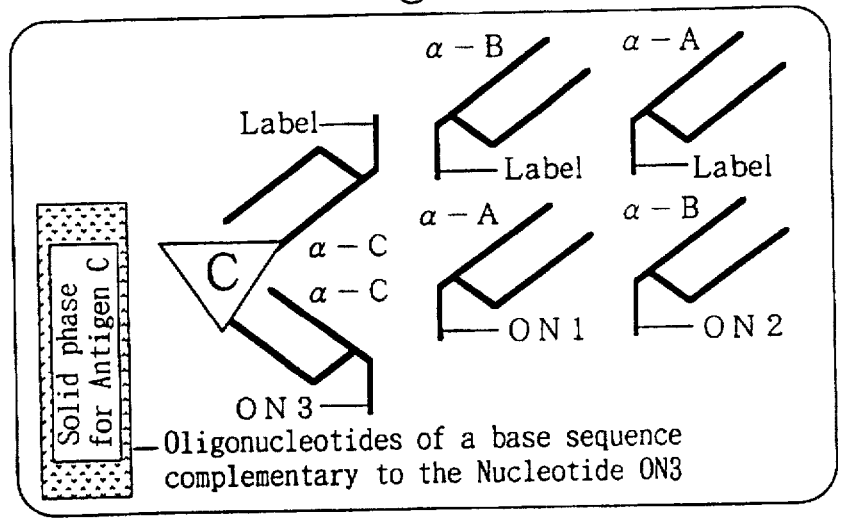
FIG. 7 depicts the state wherein a complex carrying Antigen C is captured through the complementary pairing of nucleotides onto the Solid phase for Antigen C in accordance with the present invention.
Figure 8:
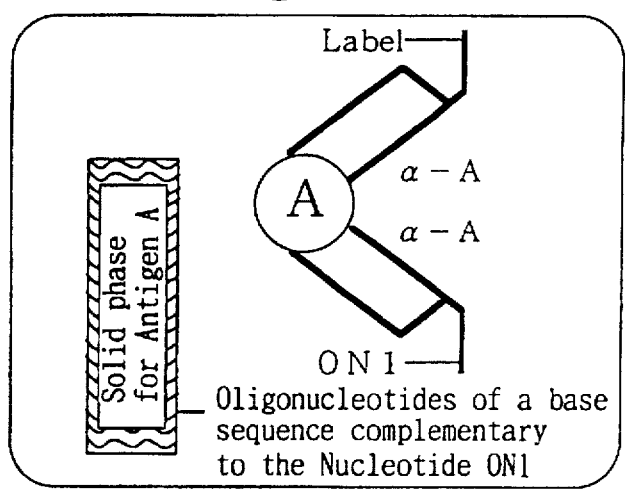
FIG. 8 depicts the state of the complex carrying Antigen A, complementarily paired onto the Solid phase for Antigen A, after washing.
Figure 9:
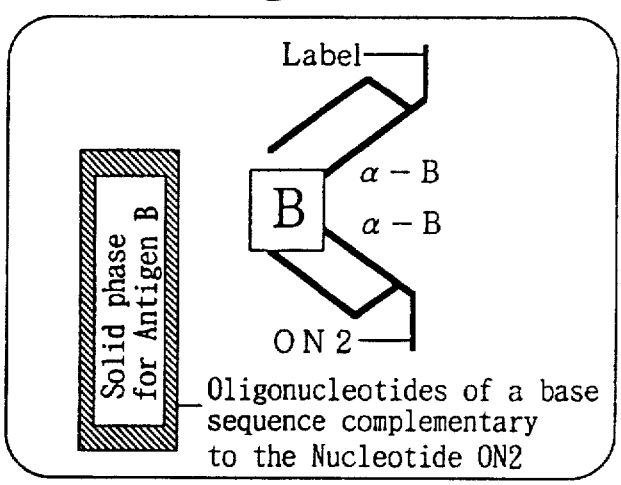
FIG. 9 depicts the state of the complex carrying Antigen B, complementarily paired onto the solid phase for Antigen B, after washing.
Figure 10:
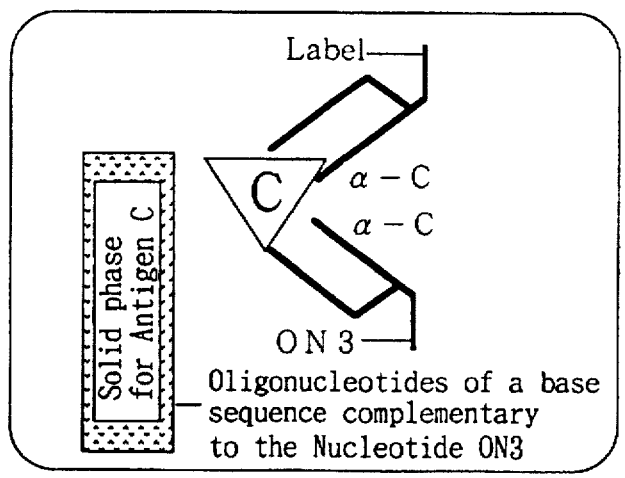
FIG. 10 depicts the state of the complex carrying Antigen C, complementarily paired onto the Solid phase for Antigen C, after washing.
Figure 13:
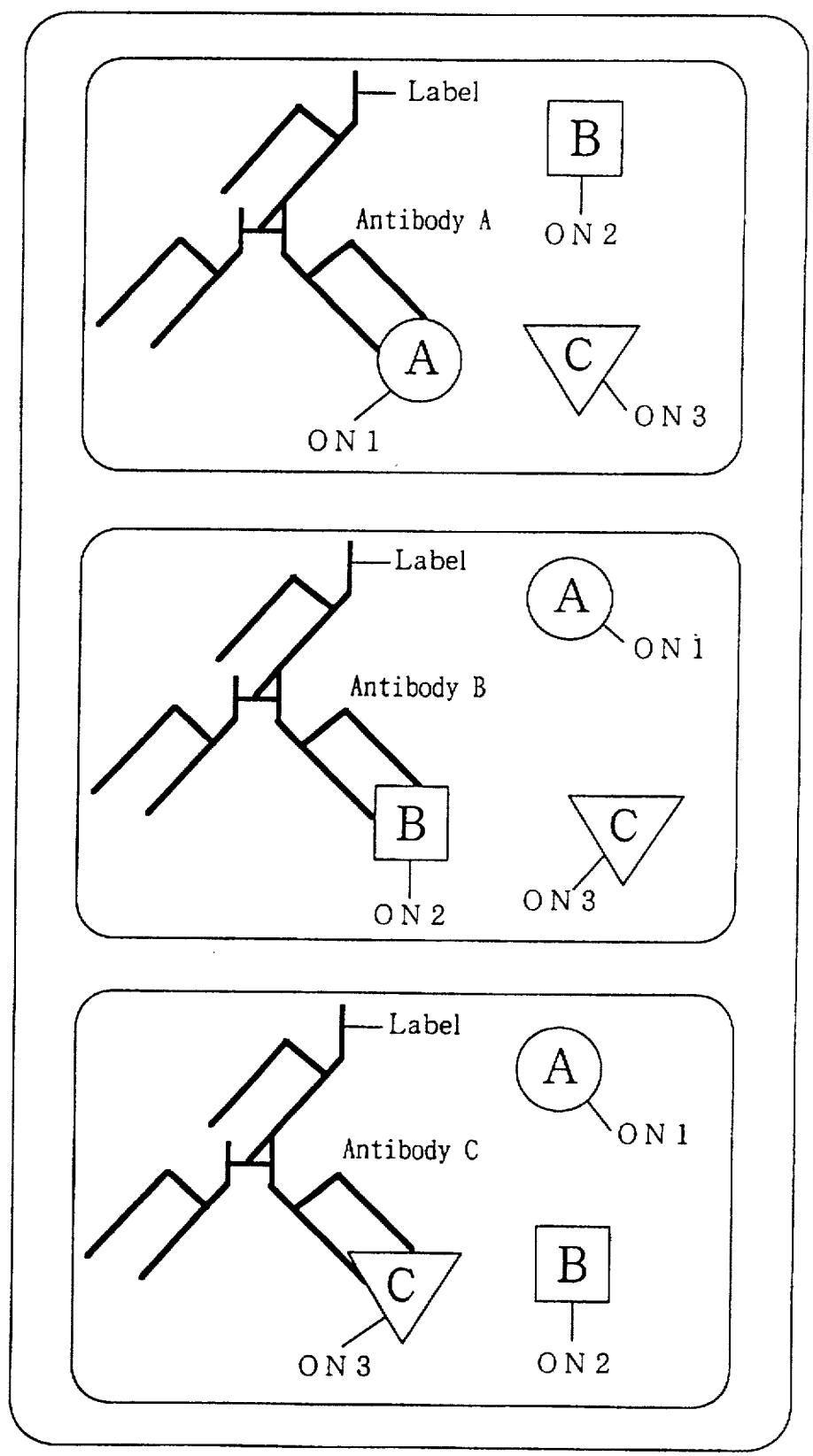
FIG. 13 depicts how the complex of (antigen-nucleotide conjugate)-antibody-labeled substance is formed, individually for Antibodies A, B and C, in a single reaction solution in accordance with the present invention.
Figure 14:
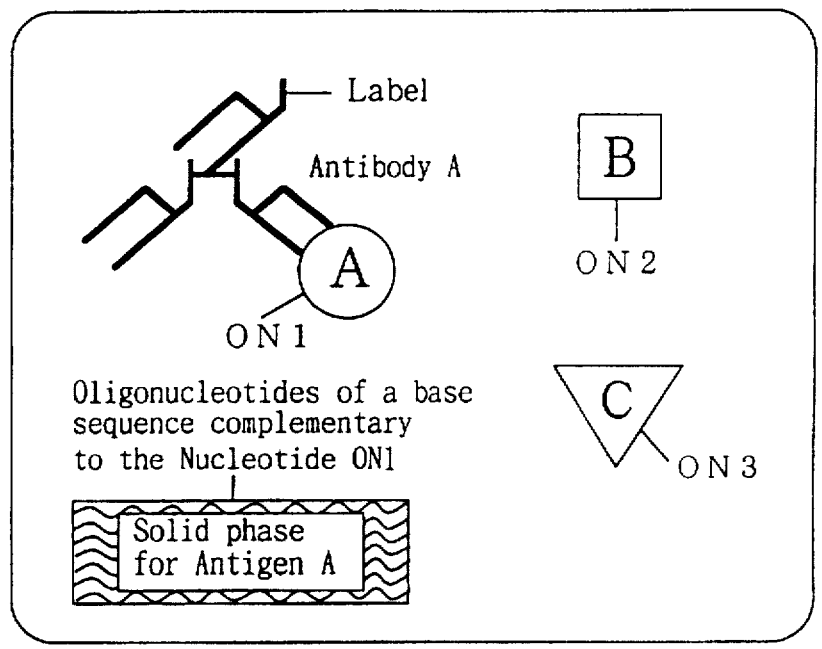
FIG. 14 depicts the state wherein a complex carrying Antibody A is captured through the complementary pairing of nucleotides onto the Solid phase for Antibody A in accordance with the present invention.
Figure 15:
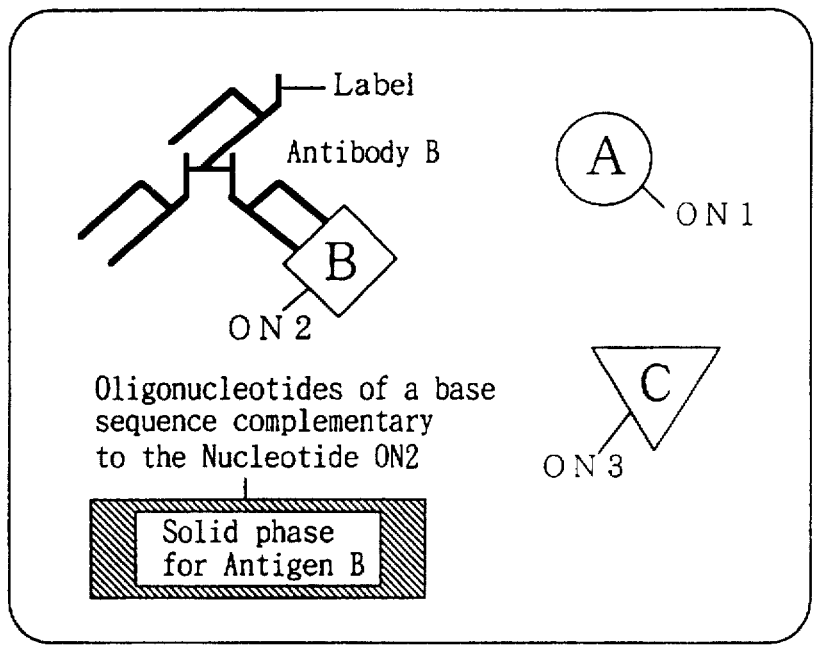
FIG. 15 depicts the state wherein a complex carrying Antibody B is captured through the complementary pairing of nucleotides onto the Solid phase for Antibody B in accordance with the present invention.
Figure 16:
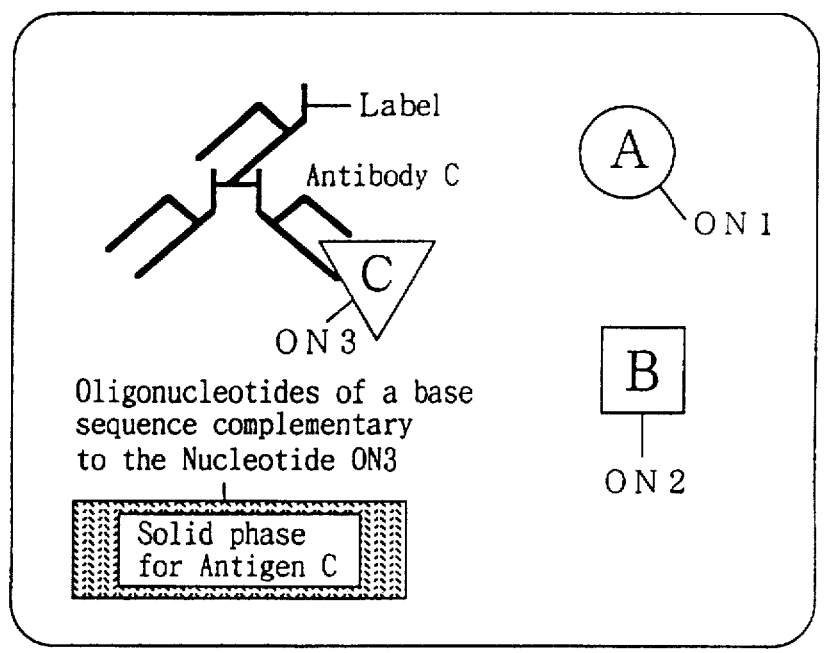
FIG. 16 depicts the state wherein a complex carrying Antibody C is captured through the complementary pairing of nucleotides onto the Solid phase for Antibody C in accordance with the present invention.
Figure 17:
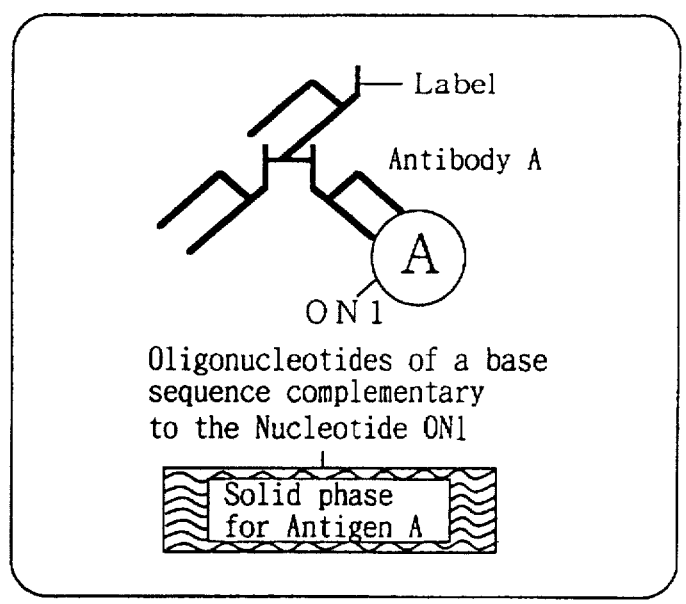
FIG. 17 depicts the state of the complex carrying Antibody A, complementarily paired onto the Solid phase for Antibody A, after washing.
Figure 18:
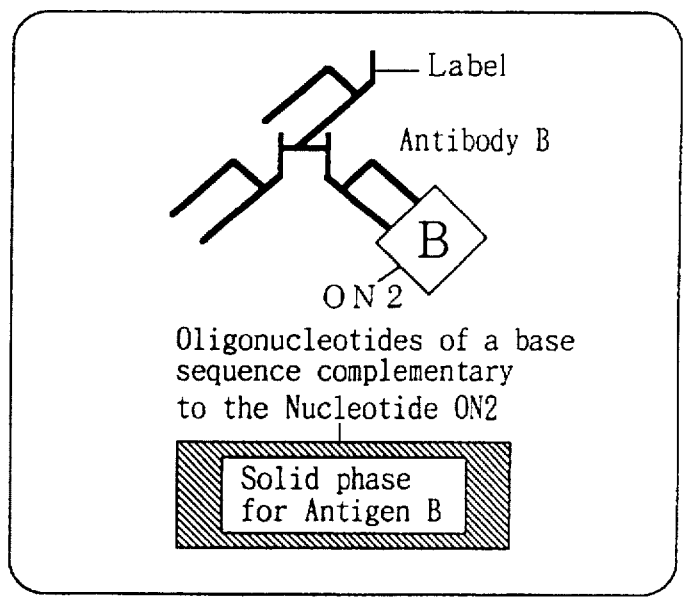
FIG. 18 depicts the state of the complex carrying Antibody B, complementarily paired onto the solid phase for Antibody B, after washing.
Figure 19:
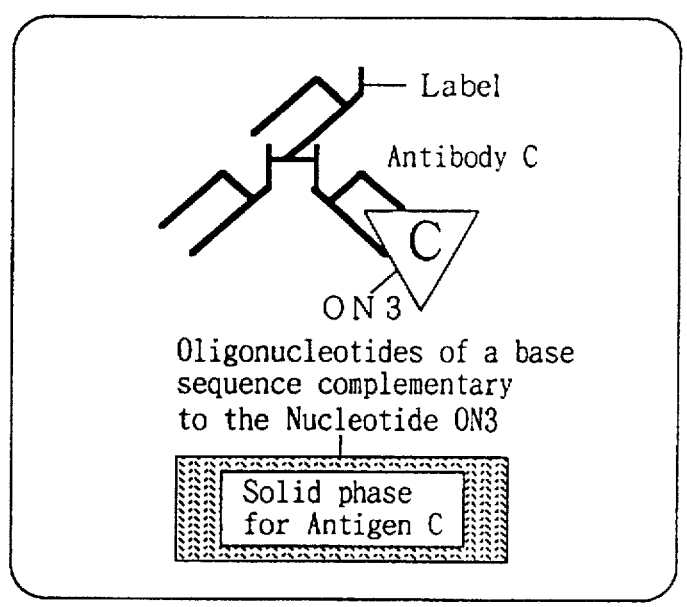
FIG. 19 depicts the state of the complex carrying Antibody C, complementarily paired onto the solid phase for Antibody C, after washing.

The following three types of oligonucleotides with an amino group at their 5' terminus were synthesized by using an automatic DNA synthesizer, Type 391A, manufactured by Applied Biosystems:

Amino group-GAA TTC CCG GGG ATC CGT CG (hereinafter referred to as "Nucleotide Pair 1(+)"); (Seq. I.D. No. 1)

Amino group-GCC AAG CTT GGC TGC AGG TC (hereinafter referred to as "Nucleotide Pair 2(+)"); (Seq. I.D. No. 2)

Amino group-AAG CTT GCA TGC CTG CAG GT (hereinafter referred to as "Nucleotide Pair 3(+)") (Seq. I.D. No. 3).

Using glutaraldehyde, these oligonucleotides were individually covalently bonded to polystyrene beads with an amino group introduced therein and were then stored in 10 mM sodium phosphate buffer and 0.1M sodium chloride, pH 7.0, containing 0.1% skimmed milk, 0.1% sodium azide and 5 mM EDTA (ethylene diamine tetraacetic acid). (Hereinafter, the solid phases individually bound with Nucleotide pairs 1(+) (Seq. I.D. No. 1), 2(+) (Seq. I.D. No. 2) and 3(+) (Seq. I.D. No. 3) are referred to as Solid Phases A, B and C, respectively.)

Rabbits were immunized individually with antigens, namely Cholera toxin (CT) generated from *Vibrio cholerae*, thermo-stable direct haemolysin (TDH) generated from *Vibrio parahaemolyticus* and *Campylobacter jejuni*, to prepare antibodies against the individual antigens. From each of the individual antibodies, the F(ab')2 was prepared from the IgG and used as the Fab', according to the method of Y. Oku, et al., Microbiol. Immunol., 32, pp. 807–816, 1988. The Nucleotide pair 1(−) having a base sequence complementary to that of the Nucleotide pair 1(+) (Seq. I.D. No. 1) was covalently bound to the anti-CT-Fab'. Similarly, the Nucleotide pair 2(−) having a base sequence complementary to that of the Nucleotide pair 2(+) (Seq. I.D. No. 2) was covalently bound to the anti-TDH-Fab'. Furthermore, the Nucleotide pair 3(−) having a base sequence complementary to that of the Nucleotide pair 3(+) (Seq. I.D. No. 3) was also covalently bound to the anti-CJ-Fab'. According to the method of Y. Oku, et al., Microbiol. Immunol., 32, pp. 807816, 1988, horseradish peroxidase (HRPO) was introduced into each of the Fab's at the SH group of their hinge components.

Using 10 mM Bicine buffer, 0.3M sodium chloride, 0.1% bovine serum albumin, 0.002% thimerosal, and 5 mM EDTA, pH 8.3, a solution containing six types of the following complexes was prepared; 20 pmol/ml Nucleotide pair 1(−) boundanti-CT-Fab', 20 pmol/ml Nucleotide pair 2(−) bound-anti-TDHFab', 20 pmol/ml Nucleotide pair 3(−) bound-anti-CJ-Fab', 800 ng/ml HRPO bound-anti-CJ-Fab', 800 ng/ml HRPO bound-anti-TDH-Fab', and 1600 ng/ml HRPO bound-anti-CJ-Fab'.

1.5 ml of the solution was individually put into each of three test tubes. Sample 1 (1.5 ml) containing 10 ng/ml CT was added into one of the tubes; Sample 2 (1.5 ml) containing 10 ng/ml TDH was added to another tube; and Sample 3 (1.5 ml) containing CJ at a 0.005 turbidity at 600 nm was added to the remaining tube. Then, the contents of these tubes were allowed to react at 37° C. for one hour.

The solution in each of the tubes was divided into 0.5 ml portions in six tubes for subsequent reaction at 37° C. for one hour; Solid phase A was added into two of the tubes; Solid phase B was added to other two tubes; and Solid phase C was added into the remaining two tubes. After discarding the reaction solution, then, the remaining solid phases were washed in 0.3M sodium chloride solution (5 ml×3 times). After washing, the individual solid phases were independently transferred into other test tubes. The HRPO attached onto each of the individual solid phases was assayed according to the method of Y. Oku, et al., Microbiol. Immunol., 32, pp. 807–816, 1988. The results are shown in Table 1 and FIG. 20.

TABLE 1

| Sample | For assaying CT | For TDH | For CJ | Results |
| --- | --- | --- | --- | --- |
| Sample 1 | 2.652 | 0.061 | 0.039 | CT |
| Sample 2 | 0.03 | 0.915 | 0.053 | TDH |
| Sample 3 | 0.068 | 0.078 | 0.357 | *C. jejuni* |

Figure 20:
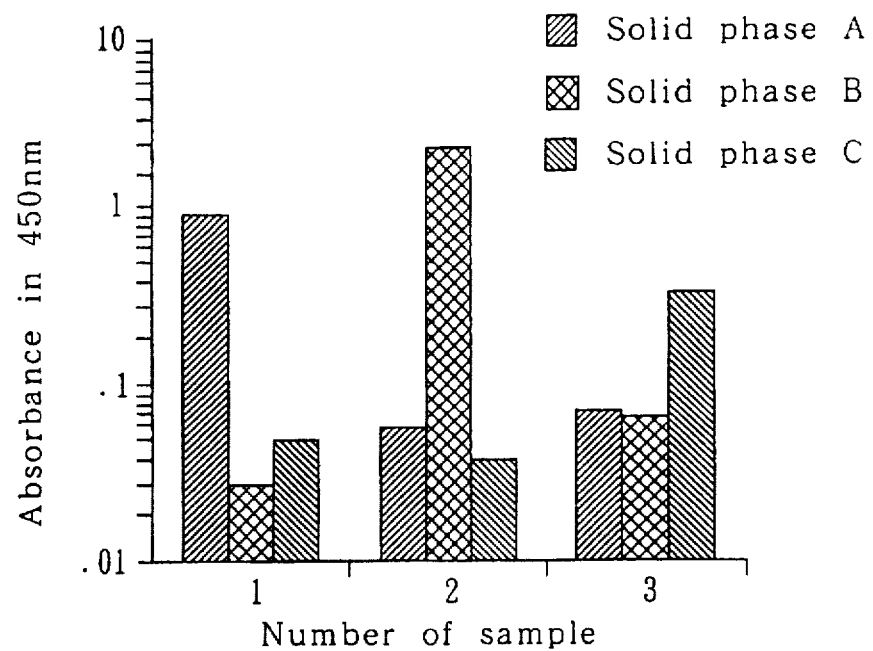
FIG. 20 is a bar graph of the absorbance of the labeled substances captured on the solid phases A, B and C, in ligands in Example 1 below.

As is apparent from Table 1 and the graph of FIG. 20, Sample 1 containing CT significantly reacts with the Solid phase A for assaying CT; and Sample 3 containing CJ significantly reacts with the Solid phase C for assaying CJ. It has been indicated that even a single reagent can assay plural species of antigens/antibodies, using the reagent and method described in the present Example. [EXAMPLE 2]

Process 1:

The following four types of oligonucleotides with an amino group at their 5' terminus were synthesized by using an automatic DNA synthesizer, Type 391A, manufactured by Applied Biosystems:

Amino group-GAA TTC CCG GGG ATC CGT CG (hereinafter referred to as "Nucleotide Pair 1(+)") (Seq. I.D. No. 1);

Amino group-AAG CTT GCA TGC CTG CAG GT (hereinafter referred to as "Nucleotide Pair 3(+)") (Seq. I.D. No. 3);

Amino group-GGC GAC TGT CGA ACC GGA AA (hereinafter referred to as "Nucleotide Pair 5(+)") (Seq. I.D. No. 4); and Amino group-CCA CCC CTA CTC CTA ATC CC (hereinafter referred to as "Nucleotide Pair 6(+)) (Seq. I.D. No. 5).

Using glutaraldehyde, these oligonucleotides were individually covalently bonded to polystyrene beads with an amino group introduced therein and were then stored in 10 mM sodium phosphate buffer and 0.1M sodium chloride, pH 7.0, containing 0.1% gelatin, 0.002% thimerosal and 5 mM EDTA (ethylene diamine tetraacetic acid).

Process 2:

A sulfhydryl group was preliminarily introduced into various types of allergens. The allergens, i.e. wheat flour, egg white, soy bean and rice, marketed for clinical tests by Torii Pharmaceutical Kabushiki Kaisha, were concentrated with cooling in ice by means of a YM-2 ultrafiltration membrane. Subsequently, these allergens were dialyzed against 0.1M sodium phosphate buffer, pH 7.0. After dialysis, an excess amount of N-succinimidyl-S-acetylthioacetate (SATA; manufactured by Pierce, Co. Ltd.) was reacted with the resulting allergens at 37° C. for one hour. After the completion of the reaction, 1M Tris-HCl buffer, pH 7.0 and 1M hydroxyamine, pH 7.0 were independently added to the individual allergen reaction products to final concentrations of 0.1M, respectively, for reaction at 37° C. for 15 minutes to promote deprotection. After the termination of the reaction, the reaction products were then applied to a gel filtration support, SEPHADEX G-25 (tradename of Pharmacia Biotechnology Group for microscopic beads of synthetic compounds derived from dextran), equilibrated with 0.1M sodium phosphate buffer, pH 6.0 containing 5 mM EDTA, to collect fractions corresponding to protein. The fractions were concentrated using the YM-2 ultrafiltration membrane, to recover four types of concentrated allergens each containing a sulfhydryl group.

Process 3:

By the same method and in the same manner, oligonucleotides having sequences complementary to those of the oligonucleotides synthesized in the Process 2 were synthesized, to recover four types of oligonucleotides each with an amino group at its 5' terminus. An oligonucleotide complementary to the Nucleotide pair 1(+) (Seq. I.D. No. 1) is designated herein as Nucleotide pair 1(−); and the other complementary oligonucleotides were designated as Nucleotide pair 3(−), Nucleotide pair 5(−) and Nucleotide pair 6(−).

Process 4:

An excess amount of N-(ε-maleimide caproyloxy) succinimide (abbreviation: EMCS) was reacted with each of the four types of the complementary oligonucleotides produced in the above Process 3 at 37° C. for one hour, to introduce the maleimide group into the 5' termini of the individual oligonucleotides. After the completion of the reaction, the four types of the oligonucleotides introduced with a maleimide group were purified through ethanol precipitation, according to a routine method.

Process 5:

The four types of the concentrated allergens introduced with a sulfhydryl group prepared in the above Process 3, were mixed with the four types of the oligonucleotides introduced with a maleimide group prepared in the Process 4, for reaction at 37° C. for one hour, to produce an allergen mixture introduced with the oligonucleotides. The wheat flour allergen was bound to the Nucleotide pair 1(−); the soy bean allergen was bound to Nucleotide pair 3(−); the egg white allergen was bound to Nucleotide pair 5(−); and the rice allergen was bound to Nucleotide pair 6(−).

Process 6:

The allergen mixture bound with the four types of the oligonucleotides, which was prepared in the above Process 5, was diluted with 10 mM sodium phosphate buffer, pH 7.0, containing 0.1% gelatin, 0.3M sodium chloride and 5 mM EDTA, to a final protein concentration of 1 µg/ml and a final concentration of anti-human IgE labeled with horseradish peroxidase to 100 ng/ml. The resulting diluted allergen mixture was defined as Reagent A. The Reagent A (7.2 ml) was poured into a test tube, followed by addition of patient serum (2.4 ml), for reaction at 37° C. for one hour. The resulting reaction solution was defined as Reagent A mixture solution. The patient serum was collected independently from three patients.

Process 7:

After the termination of the reaction, Nucleotide pair 1(+) (Seq. I.D. No. 1)-bound solid phase, Nucleotide pair 3(+)-bound solid phase, Nucleotide pair 5(+) (Seq. I.D. No. 4)-bound solid phase and Nucleotide pair 6(+) (Seq. I.D. No. 5)-bound solid phase were individually divided into test tubes, followed by addition of the Reagent A mixture solution (400 µl) after the termination of the reaction, for reaction together at 37° C. for one hour.

Process 8:

After the reaction, the resulting solution was washed off three times in 0.3M sodium chloride solution. Subsequently, the individual solid phases were transferred into fresh test tubes, where the activity of the enzyme attached onto the solid phases was assayed with 3, 3', 5, 5' tetramethylbenzidine. The assay was carried out in duplicate.

Figure 21:
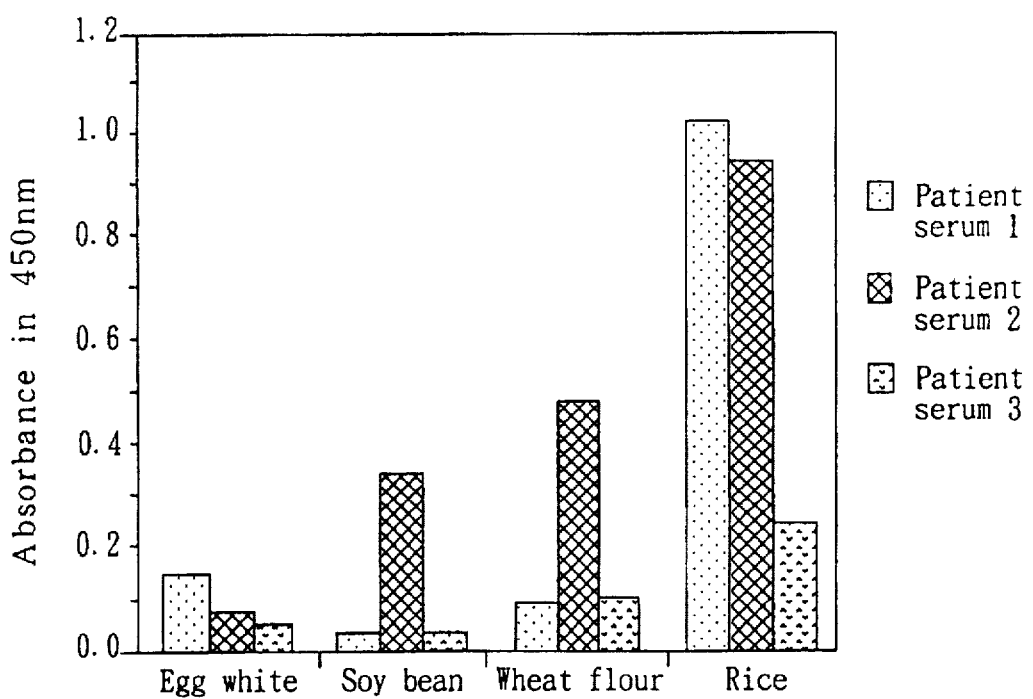
FIG. 21 is a bar graph of the absorbance of the labeled substances captured on the solid phases A, B and C, in Example 2 below.

The results are shown in the bar graphs in FIG. 21. In the graphs of FIG. 21, the abscissa represents the type of an allergen and the identity of patient serum for the individual allergens, while the ordinate represents the absorbance at 450 nm.

As is apparent from FIG. 21 with use of proteins introduced with oligonucleotides, the simultaneous detection of a plurality of allergen specific IgEs can be achieved.

In accordance with the present invention, the time required for the reaction of a mixture containing an immune complex-labeled substance with a nucleotides-bound solid phase is far shorter than the reaction time required for the antigen-antibody reaction utilizing the binding onto solid phase according to conventional methods. Thus, so-called non-specific binding of a labeled substance directly onto a solid phase can be decreased, thereby achieving a highly sensitive assay system.

In accordance with the present invention, a single reagent can detect or assay plural species of immunological ligands, namely plural species of antigens or plural species of antibodies, so the time required for detecting or assaying them can be shortened.

Theoretically, the number of combinations of base sequences between complementary nucleotides is almost infinite. Therefore, an almost infinite number of detected combinations of such immunological pairs, namely plural species of antigens or plural species of antibodies, is possible in accordance with the present invention.

---

---

We claim:

1. An assay reagent for assaying one or more ligands in a group of plural preselected ligands comprising, combined in a single admixture:

(i) a group capture reagent comprising plural conjugates including a conjugate for each of the plural preselected ligands, wherein each of said plural different conjugates comprises (1) an anti-ligand which specifically binds to its corresponding preselected ligand and (2) a preselected nucleotide sequence, wherein each conjugate of said group capture reagent comprises a different preselected nucleotide sequence; and (ii) a group labelling reagent comprising a labelled anti-ligand for each of said preselected ligands, wherein each of said labelled anti-ligands comprises (3) an anti-ligand which specifically binds to its corresponding preselected ligand and (4) a detectable label.

2. The assay reagent of claim 1 wherein each of said plural different conjugates has an anti-ligand different from the anti-ligands of other of said plural different conjugates.

3. The assay reagent of claim 1 wherein said detectable label is selected from the group consisting of an enzyme, biotin, avidin, digoxigen, a nucleotide, a metal colloid, a fluorescent compound, a luminescent compound, a metal compound and a radioisotope.

4. The assay reagent of claim 1 wherein said nucleotides are oligonucleotides.

5. The assay reagent of claim 1 wherein said anti-ligands are antigens.

6. The assay reagent of claim 1 wherein said anti-ligands are antibodies.

7. An assay kit for assaying one or more ligands in a group of plural preselected ligands, said assay kit comprising:

(i) a group capture reagent comprising plural conjugates including a conjugate for each of the plural preselected ligands, wherein each of said plural different conjugates comprises (1) an anti-ligand which specifically binds to its corresponding preselected ligand and (2) a preselected nucleotide sequence, wherein each conjugate of said group capture reagent comprises a different preselected nucleotide sequence;

(ii) a group labelling reagent comprising a labelled anti-ligand for each of said preselected ligands, wherein each of said labelled anti-ligands comprises (3) an anti-ligand which specifically binds to its corresponding preselected ligand and (4) a detectable label; and (iii) a solid phase reagent comprising a water-insoluble solid phase and a plurality of different nucleotides immobilized on said water-insoluble solid phase, each of said immobilized nucleotides being complementary to a different one of said nucleotide sequences of said conjugates in said group capture reagent.

8. The assay kit of claim 7 wherein said group capture reagent and said group labelling reagent are present combined in a single admixture.

9. An assay kit according to claim 7 wherein the anti-ligand of each of said plural different conjugates is different from the anti-ligands of other of plural different conjugates and wherein said solid phase reagent comprises a different water-insoluble solid phase substrate for each of said nucleotides immobilized thereon.

10. The assay kit of claim 7 wherein each of said immobilized nucleotides is covalently bound through its 5' terminus or its 3' terminus to said water-insoluble solid phase.

11. The assay kit of claim 7 wherein each of said immobilized nucleotides is covalently bound at a position other than its termini onto the water-insoluble solid phase.

12. The assay kit of claim 7 wherein each of said immobilized nucleotides is covalently bound to a bonding ligand and the covalently bound nucleotide-bonding ligand are physically adsorbed onto the water-insoluble solid phase.

13. The assay kit of claim 7 wherein said bonding ligand is a protein.

14. The assay kit of claim 7 wherein said detectable label is selected from the group consisting of an enzyme, biotin, avidin, digoxigen, a nucleotide, a metal colloid, a fluorescent compound, a luminescent compound, a metal compound and a radioisotope.

15. The assay kit of claim 7 wherein said nucleotides are oligonucleotides.

16. The assay kit of claim 7 wherein said anti-ligands are antigens.

17. The assay kit of claim 7 wherein said anti-ligands are antibodies.

18. An immunological assay for simultaneously assaying a liquid sample for the presence or amount of one or more ligands in a group of plural preselected ligands, comprising:

(a) providing (i) a group capture reagent comprising plural different conjugates including a conjugate for each of said plural preselected ligands, wherein each of said plural different conjugates comprises (1) an anti-ligand which specifically binds to its corresponding preselected ligand and (2) a preselected nucleotide sequence, wherein each conjugate of said group capture reagent comprises a different preselected nucleotide sequence, and (ii) a group labelling reagent comprising a labelled anti-ligand for each of said preselected ligands, wherein each of said labelled anti-ligands comprises (3) an anti-ligand which specifically binds to its corresponding preselected ligand and (4) a detectable label;

(b) contacting said sample with said group capture reagent and said group labelling reagent in a reaction solution so as to form a corresponding immune complex comprising a conjugate-ligand-label for each of said ligands which is present in said sample;

(c) separately contacting the reaction solution of step (b) with each of plural different water-insoluble solid phase substrates, each of said solid phase substrates having, immobilized thereon, only a single species of complementary nucleotide which hybridizes to its corresponding preselected nucleotide sequence, in order to separate each corresponding immune complex from the reaction solution of step (b); and (d) separately and independently measuring detectable label bound in each of said separated corresponding immune complexes in order to determine the presence or amount of each of said one or more ligands in said sample.

19. The method of claim 18 wherein said anti-ligands are antigens.

20. The method of claim 18 wherein said anti-ligands are antibodies.

* * * * *

UNITED STATES PATENT AND TRADEMARK OFFICE
CERTIFICATE OF CORRECTION

PATENT NO.  : 5,789,165
DATED       : August 4, 1998
INVENTOR(S) : OKU et al

It is certified that error appears in the above-indentified patent and that said Letters Patent is hereby corrected as shown below:

Col. 2, line 53, "IDNP" should read --DNP--.

Signed and Sealed this

Twenty-second Day of June, 1999

Attest:

Q. TODD DICKINSON

Attesting Officer      Acting Commissioner of Patents and Trademarks

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:

( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA (xi) SEQUENCE DESCRIPTION: SEQ ID NO:1:

GAATTCCGG GGATCCGTCG    20

(2) INFORMATION FOR SEQ ID NO:2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:2:

GCCAAGCTTG GCTGCAGGTC    20

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

AAGCTTGCAT GCCTGCAGGT    20

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

GGCGACTGTC GAACCGGAAA    20

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

CCACCCCTAC TCCTAATCCC    20